United States Patent [19]

Barlow

[11] 4,328,375

[45] May 4, 1982

[54] PROCESS FOR THE PRODUCTION OF ETHANOL AND/OR ACETALDEHYDE IN THE PRESENCE OF METAL COMPLEX CATALYST SYSTEMS

[75] Inventor: Michael T. Barlow, Addlestone, England

[73] Assignee: The British Petroleum Company Limited, London, England

[21] Appl. No.: 210,570

[22] Filed: Nov. 26, 1980

[30] Foreign Application Priority Data

Nov. 27, 1979 [GB] United Kingdom ............... 40843/79

[51] Int. Cl.$^3$ ........................ C07C 45/49; C07C 27/22
[52] U.S. Cl. .................................... 568/487; 568/489; 568/902
[58] Field of Search ........................ 568/487, 489, 902

[56] References Cited

U.S. PATENT DOCUMENTS 4,151,208  4/1979  Pretzer et al. ....................... 568/487
4,262,154  4/1981  Gane et al. .......................... 568/487

Primary Examiner—Werren B. Lone

Attorney, Agent, or Firm—Brooks, Haidt, Haffner & Delahunty

[57] ABSTRACT

Ethanol and/or acetaldehyde are produced by reacting at elevated temperature and pressure methanol with synthesis gas in the presence of a catalyst comprising a metal complex in which the metal is a metal of Group VIII of the Periodic Table other than iron, palladium and platinum and the ligand is derived from cyclopentadiene or a substituted cyclopentadiene and a promoter which is an iodide or a bromide. Optionally there is also added as a co-promoter a compound of formula X(A) (B) (C) wherein X is nitrogen, phosphorus, arsenic, antimony or bismuth and A, B and C are individually $C_1$ to $C_{20}$ monovalent hydrocarbyl groups which are free from aliphatic carbon-carbon unsaturation and are bound to the X atom by a carbon/X bond, or X is phosphorus, arsenic, antimony or bismuth and any two of A, B and C together form an organic divalent cyclic ring system bonded to the X atom, or X is nitrogen and all of A, B and C together form an organic trivalent cyclic ring system bonded to the X atom, e.g. triphenylphosphine.

13 Claims, No Drawings

PROCESS FOR THE PRODUCTION OF ETHANOL AND/OR ACETALDEHYDE IN THE PRESENCE OF METAL COMPLEX CATALYST SYSTEMS

The present invention relates to a process for the production of ethanol and/or acetaldehyde from methanol and a mixture of carbon monoxide and hydrogen (hereinafter to be referred to as synthesis gas) in the presence of a metal complex catalyst.

Both ethanol and acetaldehyde are valuable industrial products. Ethanol is generally manufactured either by fermentation of natural products, eg molasses or by hydration of ethylene in the presence of an acid catalyst such as phosphoric acid. Acetaldehyde is principally produced by the direct oxidation of ethylene or light hydrocarbons, and as a by-product in the production of vinyl acetate. Acetaldehyde is also produced by a vapour phase oxidation or dehydrogenation of ethanol.

The rapidly dwindling reserves of crude oil from which ethylene is derived and the associated need to utilise fully the remaining natural resources such as coal and the vast amounts of gases, eg methane, potentially available from the exploitation of North Sea oilfields has stimulated researchers to investigate other routes to ethanol utilising these materials as feedstocks. Both coal and methane gas can be converted into synthesis gas, which in turn can be reacted to form methanol, which methanol can be further reacted with carbon monoxide and hydrogen in the presence of a water soluble cobalt catalyst and under appropriate conditions to form ethanol or acetaldehyde. The course of these reactions can be represented by the following equations.

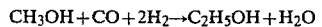

$$CH_3OH + CO + 2H_2 \rightarrow C_2H_5OH + H_2O$$

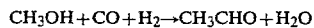

$$CH_3OH + CO + H_2 \rightarrow CH_3CHO + H_2O$$

The reaction, which is generally referred to as homologation, has been known for many years. Thus in a paper published in Science 113, 206 (1951) Wender, Friedel and Orchin reported that methanol was reacted with synthesis gas (1H$_2$:1CO) in the presence of dicobalt octacarbonyl as catalyst to produce methyl formate (2%), methyl acetate (9.0%), ethyl alcohol (38.8%), ethyl acetate (6.3%), propyl alcohol (4.7%), butyl alcohol (0.9%), methane (8.5%), propyl acetate (0.1%) and a small amount of unidentified product, the total conversion of methanol being 76.4%. Since that time many attempts to improve the yield and selectivity to ethanol have been reported. A common feature of the more recently reported work has been the addition to the cobalt catalyst of promoters such as iodides or bromides and/or organo-phosphorus compounds, eg phosphines. Furthermore it has been found that the use of arsines, stibines and bismuthines as promoters results in the production of acetaldehyde, not ethanol, as the major component of the reaction. Whilst the addition of promoters has resulted in some improvement in yield and selectivity further improvements have resulted from the addition to the initial reaction mixture of various additives as described in our Belgian Pat. No: 867548 and the published specifications of our European application Nos: 78300608.3, 79300174.4 and 78300607.5 and by the use of a polydentate ligand as described in the published specification of our European application No: 79303053.8.

Because of the inherent instability of the catalyst systems used in all the work reported to date it has been necessary to employ elevated pressures, usually a partial pressure of carbon monoxide exceeding about 70 bars, to prevent decomposition of the catalyst at the elevated temperatures required to achieve a desirable reaction rate. We have now found to our surprise that catalyst systems incorporating as an essential component certain Group VIII metal complexes in which the ligand is derived from cyclopentadiene or a substituted cyclopentadiene are at least as reactive without any loss in selectivity and are less prone to decomposition at elevated temperatures than the prior art catalyst systems hereinbefore described. It is therefore possible to achieve higher reaction rates by the use of more elevated temperatures or to use less severe reaction conditions. The stability of the catalyst system is unexpected because we would have anticipated that under the homologation reaction conditions the cyclopentadienyl ligand would be hydrogenated to cyclopentane.

Accordingly the present invention provides a process for the production of a product containing ethanol and/or acetaldehyde which process comprises reacting, at elevated temperature and pressure, methanol with synthesis gas in the presence of a catalyst comprising a metal complex in which the metal is a metal of Group VIII of the Periodic Table excluding iron, palladium and platinum and the ligand is derived from cyclopentadiene or a substituted cyclopentadiene having the formula:

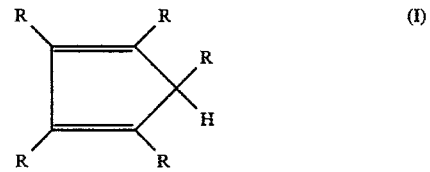

(I)

wherein one of the sbustituents R is independently methyl or ethyl and the other substituents R are independently hydrogen, methyl or ethyl, and a promoter comprising an iodide or a bromide.

The term "ligand" is used herein as defined in "Advanced Inorganic Chemistry" by F A Cotton and G Wilkinson, Wiley (US), 3rd edition 1972, which on page 139 defines a ligand as any atom, ion or molecule capable of functioning as the donor partner in one or more co-ordinate bonds.

The Periodic Table referred to throughout this specification is the Periodic Table of the Elements as published in the 44th Edition of the Handbook of Chemistry and Physics published by the Chemical Rubber Publishing Company.

Methanol is a readily available industrial product. It is generally manufactured on an industrial scale from synthesis gas. Whilst it is preferred that the methanol be substantially pure the presence of small amounts of certain impurities can be tolerated. The methanol may however contain up to 50% by weight of water.

Mixtures of the gases hydrogen and carbon monoxide are abundantly available in the form of synthesis gas. Methods for preparing synthesis gas are well known in the art and usually involve the partial oxidation of a carbonaceous substance, eg coal. Alternatively synthesis gas may be prepared, for example, by thermal steam reforming of methane. For the purpose of the present invention the molar ratio of carbon monoxide to hydrogen may suitably be in the range 2:1 to 1:3, preferably 1:1 to 1:2. Methods for adjusting the molar ratio of carbon monoxide to hydrogen are well known to those versed in the art. Although it is preferred to use substantially pure synthesis gas the presence of such impurities as carbon dioxide and nitrogen can be tolerated. On the other hand impurities having a deleterious effect on the reaction should be avoided. Thus it may be necessary in a continuously operated process to employ a gas purge to prevent the build-up of deleterious impurities.

With regard to the catalyst, suitable metals of Group VIII of the Periodic Table include cobalt, rhodium, iridium, ruthenium, nickel and osmium. Metal complexes in which the ligand is derived from cyclopentadiene or a substituted cyclopentadiene are described in 'Organometallic Compounds' by G E Coates, M L H Green and K Wade, Volume Two, 3rd Edition, Chapter 4, published by Methuen (1968). The π-cyclopentadienyl complexes in which the cyclopentadienyl ring is essentially covalently bonded to the metal, the metal being situated below the plane of the carbon atoms and usually equidistant from the five equivalent carbon atoms, are the preferred complexes. It is generally preferred to prepare the metal complex prior to carrying out the reaction. Suitable methods for preparing the metal complex are described in the aforesaid publication entitled 'Organometallic Compounds'. One such method is by the reaction, in tetrahydrofuran, of freshly prepared sodium, potassium or thallium cyclopentadienide with an anhydrous Group VIII metal halide or other suitably soluble metal salt. Alternatively the metal complex may be prepared 'in situ' under the prevailing reaction conditions by feeding a metal salt such as the halide with sodium, potassium or thallium cyclopentadienide.

With regard to the promoter the iodide or bromide can be added either in ionic form or as molecular iodine ($I_2$) or bromine ($Br_2$) or as an alkyl or aryl iodide or bromide, preferably methyl iodide. In the ionic form the iodide or bromide may be added as metal iodide or metal bromide. However, the iodide or bromide may also be added in ionic form utilising cations which are inert with regard to the hydrocarbonylation reaction. Typical of the inert form is potassium iodide or bromide, sodium iodide or bromide and lithium iodide or bromide. Of the iodide or the bromide the iodide is preferred.

The molar ratio of the metal complex to the promoter may suitably be within the range from 1:5 to 10:1, preferably from 1:2 to 5:1. The use of the metal complex catalyst and promoter according to the invention usually produces a product containing acetaldehyde as the major component and ethanol as a minor component.

In addition to the catalyst and the promoter there may also be added as a co-promoter a compound having the general formula:

(II)

wherein X is nitrogen, phosphorus, arsenic, antimony or bismuth and A, B and C are individually monovalent hydrocarbyl groups containing from 1 to 20 carbon atoms which hydrocarbyl groups are free from aliphatic carbon—carbon unsaturation and are bound to the X atom by a carbon/X bond, or X is phosphorus, arsenic, antimony or bismuth and any two of A, B and C together form an organic divalent cyclic ring system bonded to the X atom, or X is nitrogen and all of A, B and C together form an organic trivalent cyclic ring system bonded to the X atom.

Preferred compounds having the formula (II) are those in which X is nitrogen, phosphorus, arsenic, antimony or bismuth and A, B and C are independently monovalent hydrocarbyl groups. The hydrocarbyl groups may suitably be substituted or unsubstituted saturated aliphatic groups, saturated cyclo-aliphatic groups or aromatic groups, of which the unsubstituted groups are preferred.

Examples of suitable compounds having the formula (II) are triphenylamine, triphenylphosphine, triphenylarsine, triphenylstibine, triphenylbismuth, triethylphosphine, tri-n-butylphosphine, tri-t-butylphosphine, tricyclohexylphosphine, tris (4-tolyl) phosphine, tris (3-chlorophenyl) phosphine, diphenylhexylphosphine, dibutyloctadecylphosphine, tribenzylphosphine, pyridine, diphenylamine and tri-n-butylarsine. Preferred compounds having the formula (II) are triphenylphosphine, triethylphosphine and tri-n-butylphosphine.

Alternatively the co-promoter may be a polydentate ligand wherein the donor atoms are either identical or combinations of dissimilar atoms of the elements nitrogen, phosphorus, arsenic, antimony or bismuth, with the proviso that no two of the atoms are directly bonded to each other. Suitable such polydentate ligands are described in our published UK application No: 79303053.8. Preferably the polydentate ligand is a compound having the formula:

$$R^1R^2(X)—(CR^5R^6)n-Y(R^3)(R^4)$$ (III)

wherein X and Y are independently nitrogen, phosphorus, arsenic, antimony or bismuth, n is an integer, $R^1$, $R^2$, $R^3$ and $R^4$ are independently hydrocarbyl groups containing from 1 to 20 carbon atoms as defined in the compound of formula (II) and $R^5$ and $R^6$ are either hydrogen atoms or hydrocarbyl groups containing from 1 to 20 carbon atoms as defined for the compound of formula (II).

Illustrative of suitable compounds of formula (III) which may be used as the co-promoter are $(C_6H_5)_2P(CH_2)P(C_6H_5)_2$; $(C_6H_5)_2P(CH_2)_4P(C_6H_5)_2$ and $(C_6H_5)_2P(CH_2)_6P(C_6H_5)_2$.

The molar ratio of the metal complex to the co-promoter may suitably be in the range 1:1 to 1:10, preferably 1:1 to 1:3.

The term "hydrocarbyl" has been used throughout the foregoing in its accepted meaning as representing a radical formed from a hydrocarbon by removal of a hydrogen atom.

In addition to the catalyst a co-catalyst may also be used. Suitably the co-catalyst may be a soluble compound, eg a halide, of one or more other metals of Group VIII of the Periodic Table. Suitable metals of Group VIII include ruthenium, osmium, platinum, palladium, iridium and rhodium. The metal may be added for example in the form of a carbonyl eg $Ru_3(CO)_{12}$, a beta-diketonate eg Ru (acetoacetonate)$_3$, a halide eg $RuCl_3.3H_2O$ or a salt of a carboxylic acid eg ruthenium acetate. The molar ratio of the catalyst to the co-catalyst may be in the range 2:1 to 100:1, preferably 10:1 to 20:1. Using a co-catalyst the product distribution is shifted in the direction of ethanol as the major product and acetaldehyde as the minor product.

Conditions of elevated temperature and pressure which may suitably be used are a temperature in the range 145° to 210° C., preferably 170° to 195° C. and a pressure in the range 1 to 300 bars, preferably 50 to 200 bars.

The process may be carried out batchwise or continuously, continuous operation being preferred. The process may be carried out continuously for example by continuously feeding methanol and synthesis gas to a reactor containing the catalyst, removing from the reactor a liquid product containing ethanol and/or acetaldehyde, by-products, unchanged methanol, catalyst and unreacted synthesis gas, separating the synthesis gas which may be recycled to the reactor, removing light ends including ethers, separating the product containing ethanol and/or acetaldehyde and by-products from the catalyst and thereafter recovering ethanol and/or acetaldehyde from the by-products, there being recycled to the reactor the catalyst and methanol. Other reaction by-products particularly those which can act as precursors for the formation of ethanol and/or acetaldehyde may also be recycled to the reactor with advantage. It may be necessary to feed from time to time further catalyst.

The residence time may suitably be up to 8 hours, but is preferably in the range of from 20 to 200 minutes. Short residence times are preferred because long residence times may lead to further reaction of acetaldehyde by aldol condensation-type reaction giving, for example, n-butyraldehyde. Within the context of the specification the residence time for batchwise operation is that time during which the reactor is at the specified reaction temperature. When the process is operated continuously the residence time is calculated as follows:

Residence Time (Hours) =
$$\frac{\text{Volume of the reactor occupied by the liquid phase at } STP \text{ (liters)}}{\text{Total flow of liquid into the reactor (liters/hour } STP\text{)}}$$

With regard to the various ratios of reactants to be employed in the process of the invention it has already been stated that the methanol may contain up to 50% by weight of water. The molar ratio of methanol to synthesis gas fed in both continuous and batch operation may be in the range of from 10:1 to 1:20, preferably from 2:1 to 1:5. The molar ratio of the catalyst to methanol may be in the range 1:10 to 1:1000, preferably from 1:4 to 1:800.

The invention will now be illustrated by the following Examples and Comparison Tests in which terms such as 'the total realisable yield of ethanol (acetaldehyde)', 'the % Molar Yield of Realisable Ethanol (Acetaldehyde)', '% Molar Selectivity to Realisable Ethanol (Acetaldehyde)' and '% Methanol conversion' are used. These are defined as follows:

The total realisable yield of ethanol is defined as the yield of free ethanol plus with yield of ethanol realisable by the hydrolysis of ethanol-yielding esters (eg ethyl acetate). In the same way total realisable yield of acetaldehyde is defined as the yield of free acetaldehyde plus the yield of acetaldehyde realisable by the hydrolysis of acetaldehyde-yielding compounds (eg dimethylacetal) and realisable methanol is defined as the free methanol plus the methanol realisable by the hydrolysis of methanol-yielding esters (eg methyl acetate). Thus, % Molar Yield of Realisable Ethanol (Acetaldehyde) =
$$\frac{\text{Moles of realisable methanol converted into realisable ethanol (acetaldehyde)} \times 100}{\text{Total moles of realisable methanol fed}}$$

and,

% Molar Selectivity to Realisable Ethanol (Acetaldehyde) =
$$\frac{\text{Moles of realisable methanol converted into realisable ethanol (acetaldehyde)} \times 100}{\text{Total moles of realisable methanol converted}}$$

By the yield of realisable acetic acid is meant the yield of free acetic acid plus the yield of acetic acid realisable by the hydrolysis of acetic acid-yielding esters (eg methyl acetate). In calculating the yield it is assumed that all the acetic acid is derived from methanol and synthesis gas.

Thus,

% Molar Yield of Realisable Acetic Acid =
$$\frac{\text{Moles of realisable methanol converted into realisable acetic acid} \times 100}{\text{Total moles of realisable methanol fed}}$$

% Methanol conversion =
$$\frac{\text{Total moles of methanol converted}}{\text{Total moles of methanol fed}} \times 100$$

CATALYST COMPOSITIONS

Composition A

The components were mixed in the following proportions:

| | |
|---|---|
| Cyclopentadienyl cobalt dicarbonyl | 4.49g (0.025 moles) |
| Iodine | 3.17g (0.0125 moles) |
| Triphenylphosphine | 6.50g (0.025 moles) |

Composition B

The components were mixed in the following proportions:

| | |
|---|---|
| Cobalt acetate | 6.2g (0.025 moles) |
| Iodine | 3.17g (0.0125 moles) |
| Triphenylphosphine | 6.50g (0.025 moles) |

Composition B is not suitable for use in the process of the present invention because it lacks a metal complex catalyst.

Composition C

The components were mixed in the following proportions:

| | |
|---|---|
| Bis (cyclopentadienyl) cobalt | 1.4 g (0.07 moles) |
| Iodine | 1.3 g (0.005 moles) |
| Triphenylphosphine | 1.8 g (0.007 moles) |

Composition D

The components were mixed in the following proportions:

| | |
|---|---|
| Pentamethylcyclopentadienyl cobalt dicarbonyl | 0.9 g (0.004 moles) |
| Iodine | 0.5 g (0.002 moles) |
| Triphenylphosphine | 1.04g (0.004 moles) |

| | -continued | |
|---|---|---|
| Ruthenium triiodide | | 0.72g (0.0015 moles) |

Methanol Hydrocarbonylation

Example 1

A stainless-steel, magnetically-stirred autoclave equipped for high-pressure reactions, was charged with Composition A and 64.0 g (2.0 moles) of commercial methanol. After purging with nitrogen, the autoclave was pressurised with a 1:1 mixture of carbon monoxide and hydrogen (to about 100 bars). The reactor temperature was rapidly raised to 190° C. and the pressure adjusted to 200 bars. After two hours the autoclave was cooled to room temperature, and the reaction products analysed by gas-liquid chromotography (GLC). The reaction conditions and the product distribution is given in the following Table. In addition to the products listed in the Table varying amounts of dimethyl ether, 1,1-dimethoxyethane, n-butyraldehyde, carbon dioxide and methane were found as by-products.

Example 2

Example 1 was repeated with the exception that the pressure at which the autoclave was maintained was changed from 200 bars to 150 bars.

Example 3

Example 1 was repeated with the exception that the pressure at which the autoclave was maintained was changed from 200 bars to 100 bars.

Comparison Test 1

Example 1 was repeated with the exception that Composition A was replaced by Composition B.

This is not an example according to the invention and is included only for the purpose of comparison.

Comparison Test 2

Example 3 was repeated with the exceptions that Catalyst A was replaced by Catalyst B and the temperature was reduced to 185° C.

This is not an example according to the invention and is included only for the purpose of comparison.

Comparison Test 3

Comparison Test 1 was repeated with the exception that 1.64 g (0.0062 moles) ruthenium trichloride was added to Composition B.

This is not an example according to the invention and is included only for the purpose of comparison.

Example 4

Example 1 was repeated except that 1.64 g (0.0062 moles) of ruthenium trichloride was added to Composition A.

Example 5

Example 3 was repeated except that 2.94 g (0.0062 moles) ruthenium triiodide was added to Composition A and the temperature was increased to 200° C.

Example 6

Example 5 was repeated except that the temperature was reduced to 190° C.

Example 7

Example 6 was repeated except that the temperature was reduced to 185° C.

Example 8

Example 1 was repeated except that the triphenylphosphine was omitted from Composition A.

Example 9

Example 1 was repeated except that Composition C was used in place of Composition A.

Example 10

Example 3 was repeated except that Composition D was used in place of Composition A and the temperature was 185° C., not 190° C.

Example 11

Example 3 was repeated except that a 2:1 mixture of carbon monoxide and hydrogen was used in place of the 1:1 mixture.

The reaction conditions and the product distributions for Examples 2 to 11 are given in the following Table.

TABLE

| | | | | % | % Molar yield on $CH_3OH$ fed | | | |
|---|---|---|---|---|---|---|---|---|
| Example | Catalyst Composition | T (°C.) | P (bar) | $CH_3OH$ conv | Realisable $C_2H_5OH$ | Realisable $CH_3CO_2H$ | Realisable $CH_3CHO$ | higher alcohols |
| 1 | A | 190 | 200 | 67.0 | 24.1 | 9.2 | 6.4 | 0.5 |
| 2 | A | 190 | 150 | 40.8 | 15.6 | 6.1 | 2.5 | 3.2 |
| 3 | A | 190 | 100 | 22.3 | 3.9 | 2.3 | 5.0 | 0.7 |
| Comp Test 1 | B | 190 | 200 | 68.0 | 22.8 | 10.4 | 3.1 | 3.3 |
| Comp Test 2 | B | 185* | 100 | 22.9 | — | 3.2 | 5.1 | — |
| Comp Test 3 | B + $RuCl_3$ | 190 | 200 | 46.8 | 29.0 | 4.7 | — | 2.0 |
| 4 | A + $RuCl_3$ | 190 | 200 | 59.9 | 32.4 | 4.1 | 0.3 | 1.4 |
| 5 | A + $RuI_3$ | 200 | 100 | 54.7 | 13.2 | 3.0 | 0.2 | 0.2 |
| 6 | A + $RuI_3$ | 190 | 100 | 46.9 | 19.2 | 4.9 | 0.7 | 0.3 |
| 7 | A + $RuI_3$ | 185 | 100 | 44.5 | 20.9 | 5.3 | 0.5 | 0.4 |
| 8 | A** | 190 | 200 | 82.0 | 16.7 | 4.5 | 0.5 | 0.1 |
| 9 | C | 190 | 200 | 57.5 | 0.3 | 2.5 | 15.9 | — |
| 10 | D | 185 | 100 | 34.1 | 10.6 | 3.1 | 2.1 | — |
| 11 | A | 185 | 100 | 28.1 | 9.1 | 8.2 | 1.1 | — |

**contains no triphenylphosphine.
*Catalyst B decomposes rapidly above 185° C. at a pressure of 100 bars.

With reference to the Table it can be seen that whereas the prior art catalyst composition used in Comparison Test 2 decomposes at 185° C. and 100 bars and yields no ethanol the cyclopentadienyl cobalt catalyst composition as used in Examples 3 and 7, the bis (cyclopentadienyl) cobalt catalyst composition as used in Example 9 and the pentamethylcyclopentadienyl cobalt dicarbonyl catalyst composition as used in Example 10 are stable and active under similar conditions. Under similar conditions and in the presence of ruthenium as co-catalyst the process of the invention results in a higher methanol conversion and ethanol yield (Example 4) than the prior art process (Comparison Test 3).

I claim:

1. A process for the production of a product containing ethanol and/or acetaldehyde which process comprises reacting, at elevated temperature and pressure, methanol with synthesis gas in the presence of a catalyst comprising a metal complex in which the metal is a metal of Group VIII of the Periodic Table excluding iron, palladium and platinum and the ligand is derived from cyclopentadiene or a substituted cyclopentadiene having the formula:

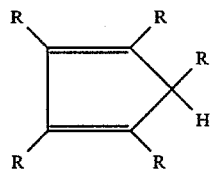 (I)

wherein one of the substituents R is independently methyl or ethyl and the other substituents R are independently hydrogen, methyl or ethyl, and a promoter comprising an iodide or a bromide.

2. A process according to claim 1 wherein the metal of Group VIII of the Periodic Table is cobalt, rhodium, iridium, ruthenium, nickel or osmium.

3. A process according to claim 1 or claim 2 wherein the metal complex is a π-cyclopentadienyl complex.

4. A process according to claim 1 wherein the promoter is molecular iodine.

5. A process according to claim 1 wherein the molar ratio of the metal complex to the promoter is in the range from 1:5 to 10:1.

6. A process according to claim 1 wherein there is also added a co-promoter which is a compound having the general formula:

 (II)

wherein X is nitrogen, phosphorus, arsenic, antimony or bismuth and A, B and C are individually monovalent hydrocarbyl groups containing from 1 to 20 carbon atoms which hydrocarbyl groups are free from aliphatic carbon-carbon unsaturation and are bound to the X atom by a carbon/X bond, or X is phosphorus, arsenic, antimony or bismuth and any two of A, B and C together form an organic divalent cyclic ring system bonded to the X atom, or X is nitrogen and all of A, B and C together form an organic trivalent cyclic ring system bonded to the X atom.

7. A process according to claim 6 wherein the co-promoter is triphenylphosphine, triethylphosphine or tri-n-butylphosphine.

8. A process according to claim 1 wherein there is also added a co-promoter which co-promoter is a polydentate ligand having the formula:

$$R^1R_2(X)-(CR^5R^6)_n-Y(R^3)(R^4)$$ (III)

wherein X and Y are independently nitrogen, phosphorus, arsenic antimony or bismuth, n is an integer, $R^1$, $R^2$, $R^3$, and $R^4$ are independently hydrocarbyl groups containing from 1 to 20 carbon atoms and $R^5$ and $R^6$ are either hydrogen atoms or hydrocarbyl groups containing from 1 to 20 carbon atoms.

9. A process according to claim 8 wherein the polydentate ligand is $(C_6H_5)_2P(CH_2)P(C_6H_5)_2$, $(C_6H_5)_2P(CH_2)_4P(C_6H_5)_2$ or $(C_6H_5)_2P(CH_2)_6P(C_6H_5)_2$.

10. A process according to claim 6 wherein the molar ratio of the metal complex to the co-promoter is in the range from 1:1 to 1:3.

11. A process according to claim 1 wherein there is also added a co-catalyst which is a soluble compound of one or more other metals of Group VIII of the Periodic Table.

12. A process according to claim 1 wherein the elevated temperature is in the range from 145° to 210° C. and the pressure is in the range from 1 to 300 bars.

13. A process according to claim 12 wherein the temperature is in the range from 170° to 195° C. and the pressure is in the range from 50 to 200 bars.

* * * * *

UNITED STATES PATENT AND TRADEMARK OFFICE
CERTIFICATE OF CORRECTION

PATENT NO. : 4,328,375
DATED : May 4, 1982
INVENTOR(S) : MICHAEL T. BARLOW

It is certified that error appears in the above—identified patent and that said Letters Patent is hereby corrected as shown below:

In the Table at cols. 7 and 8, under the heading "Realisable $CH_3CHO$", change "2.1" next to Example 10, to --2.2--.

Col. 10, claim 8, in formula "(III)", change "$R_2$" to --$R^2$--.

Signed and Sealed this

Seventh Day of December 1982

[SEAL]

Attest:

GERALD J. MOSSINGHOFF

Attesting Officer                Commissioner of Patents and Trademarks